(12) United States Patent
Manyam et al.

(10) Patent No.: US 8,335,558 B2
(45) Date of Patent: Dec. 18, 2012

(54) METHOD AND APPARATUS FOR DETECTING, CHARACTERIZING, AND SAMPLING TISSUE VIA A LUMEN

(75) Inventors: Harish Manyam, Pittsburgh, PA (US); Robert Biederman, Wexford, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 426 days.

(21) Appl. No.: 12/583,987

(22) Filed: Aug. 28, 2009

(65) Prior Publication Data

US 2011/0054302 A1 Mar. 3, 2011

(51) Int. Cl.
*A61B 5/05* (2006.01)
(52) U.S. Cl. ........ 600/427; 600/424; 600/407; 600/449; 600/160
(58) Field of Classification Search .................. 600/407, 600/427, 441, 449, 437, 181, 160, 473, 475, 600/476, 477, 478
See application file for complete search history.

(56) References Cited

U.S. PATENT DOCUMENTS

| | | | |
|---|---|---|---|
| 2002/0026127 A1* | 2/2002 | Balbierz et al. | 600/567 |
| 2009/0012422 A1* | 1/2009 | Marban | 600/564 |

\* cited by examiner

*Primary Examiner* — Brian Casler
*Assistant Examiner* — Joel Lamprecht
(74) *Attorney, Agent, or Firm* — Fox Rothschild LLP

(57) ABSTRACT

An apparatus for diagnosing a patient includes a catheter having a tip. The apparatus includes a bioptome disposed in proximity to the tip to obtain a tissue sample of the patient. The apparatus includes a radiodetector disposed in proximity to the tip to detect radiation in the patient. A method for diagnosing a patient includes the steps of moving a tip of a catheter to a desired location in a blood vessel of the patient determined by radiation detected by a radiodetector disposed in proximity to the tip. There is the step of obtaining a tissue sample of the patient with a bioptome disposed in proximity to the tip.

8 Claims, 4 Drawing Sheets

METHOD AND APPARATUS FOR DETECTING, CHARACTERIZING, AND SAMPLING TISSUE VIA A LUMEN

FIELD OF THE INVENTION

The present invention is related to a catheter with a bioptome which obtains a tissue sample of the patient and radiodetector disposed in proximity to the tip to detect radiation in the patient. (As used herein, references to the "present invention" or "invention" relate to exemplary embodiments and not necessarily to every embodiment encompassed by the appended claims.) More specifically, the present invention is related to a catheter with a bioptome which obtains a tissue sample of the patient and radiodetector disposed in proximity to the tip to detect radiation in the patient to obtain the tissue sample at a location of highest radiation in the patient.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Disease processes have been hard to diagnose. The problem in their diagnosis is not the ability to detect that there is a disease process, but which disease process is causing the symptoms. This is likely because these processes are contained to a certain area and we have little information to diagnose them without a sample of the tissue affected. There are a variety of techniques available that try to undertake this process of diagnosis. However, these techniques are limited by their ability to only locate the site affected.

Only an invasive test, such as a myocardial biopsy, which is done after the diagnosis is hypothesized by visualizing the disease process can offer an absolute answer. We, however, are still limited in the use of this specific tissue diagnosis since we are not able to visualize the disease site affected while sampling that site leading to a poor sensitivity of taking these samples. There are areas accessible via a lumen that needs to be accessed to evaluate an area of interest. These areas of interest, specifically in the body, may also need to be sampled.

Currently, there is a technique available to invasively detect atherosclerosis. This technique employs a radiodetector on the tip of a catheter which detects metabolic activity by the use of a radiotracer. This has the greatest benefit for angiography in decision making for intervention.

However, decision making for non atherosclerotic myocardial pathologies is more problematic. After an array of noninvasive strategies to increase the pre-test probability of diagnosing these disease processes we are still left with relatively blind invasive techniques such as a myocardial biopsy as a diagnostic strategy. A variety of limitations to this blind invasive strategy are 1) the heterogeneity of the underlying pathology, 2) sampling bias/error, 3) operator limitation, and 4) need for multiple myocardial biopsies due to the above limitations.

Thus, a technique that could combine the existing radiotracer techniques with a myocardial bioptome to improve the precision of myocardial sampling too would potentially markedly decrease the number of samples, morbidity, and mortality while improving the diagnostic accuracy.

Currently, there is a technique that allows uptake of radiolabeled particles, in this case glucose into cells, and allows a catheter that detects these particles.

Patent: EP1220691

Title: Methods and apparatus for characterizing lesions in blood vessels and other body lumens. The patent involves characterizing lesions and other target sites within body lumens. It relies on introducing a radiolabeled marker that localizes to the lesion, or site of interest. The marker is then quantified by the introduction of a detector into a body lumen. This patent only allows location and characterization of the lesion of interest however it does not allow sampling to provide a definitive diagnosis.

The present invention relies on using a labeled marker, specifically a radiolabeled tracer, to localize the area(s) of interest. The marker would be administered systemically into the blood stream through the subject's vasculature. The uptake of the marker would be measured by the detector to localize the area of interest. A catheter which would be equipped with a detector and a bioptome would enable access to the area of interest. The catheter would be attached to a processor which would provide readout of the area of interest in order to provide appropriate localization of the site.

BRIEF SUMMARY OF THE INVENTION

The present invention modifies this catheter by adding a biopsy needle or bioptome to the end of the catheter device to allow not only to find the specific location of the disease process but also to take a sample of the material to confirm the appropriate site and pathology of the disease process to aid in treatment. The biopsy catheter would lie at the end of the detector and allow sampling of the actual site allowing precise diagnosis. The present invention would involve miniaturization of the current catheter in French size to incorporate the bioptome as well.

The present invention pertains to an apparatus for diagnosing a patient. The apparatus comprises a catheter having a tip. The apparatus comprises a bioptome disposed in proximity to the tip to obtain a tissue sample of the patient. The apparatus comprises a radiodetector disposed in proximity to the tip to detect radiation in the patient.

The present invention pertains to a method for diagnosing a patient. The method comprises the steps of moving a tip of a catheter to a desired location in a blood vessel of the patient determined by radiation detected by a radiodetector disposed in proximity to the tip. There is the step of obtaining a tissue sample of the patient with a bioptome disposed in proximity to the tip.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 1:
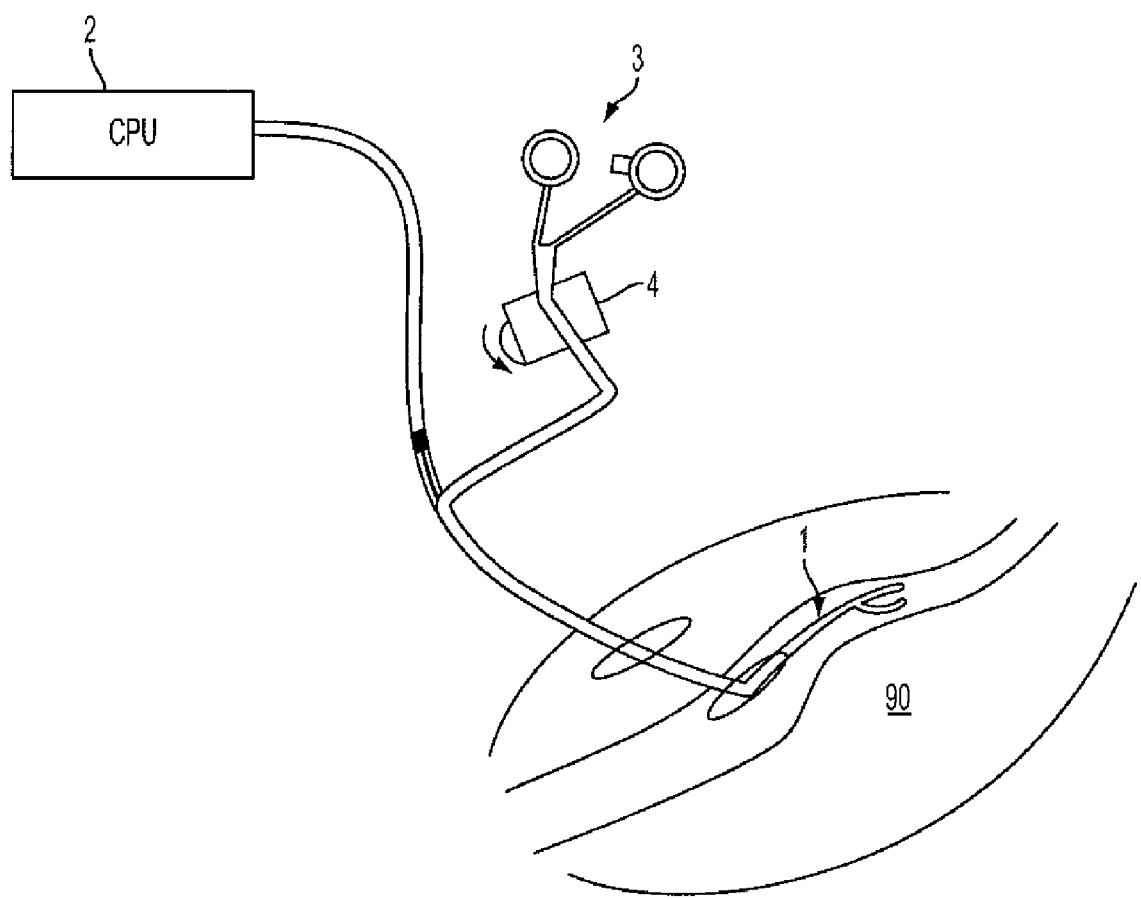
FIG. 1 is a representation of the apparatus of the present invention.

Referring now to the drawings wherein like reference numerals refer to similar or identical parts throughout the several views, and more specifically to FIGS. 1-4 thereof, there is shown an apparatus 50 for diagnosing a patient. The apparatus 50 comprises a catheter 1 having a tip. The apparatus 50 comprises a bioptome 52 disposed in proximity to the tip to obtain a tissue sample of the patient. The apparatus 50 comprises a radiodetector 5 disposed in proximity to the tip to detect radiation in the patient.

Figure 2:
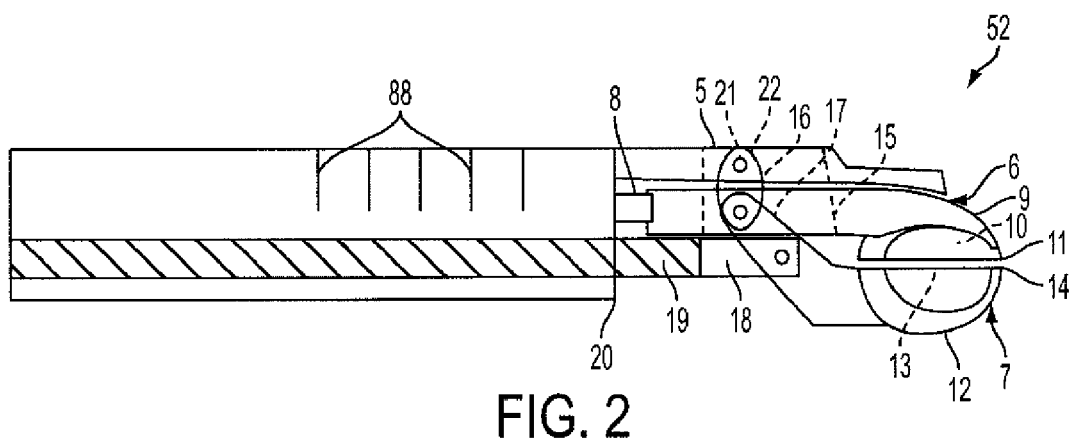
FIG. 2 is a representation of the tip of the apparatus.
Figure 3:
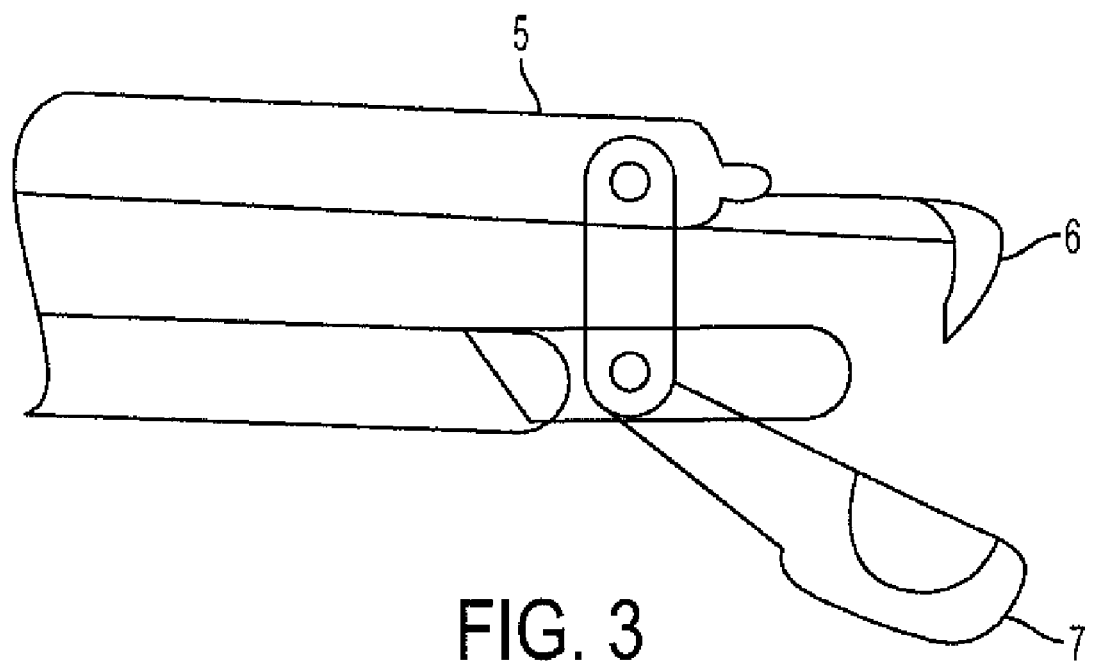
FIG. 3 is a representation of the upper and lower jaws of the apparatus.
Figure 4:
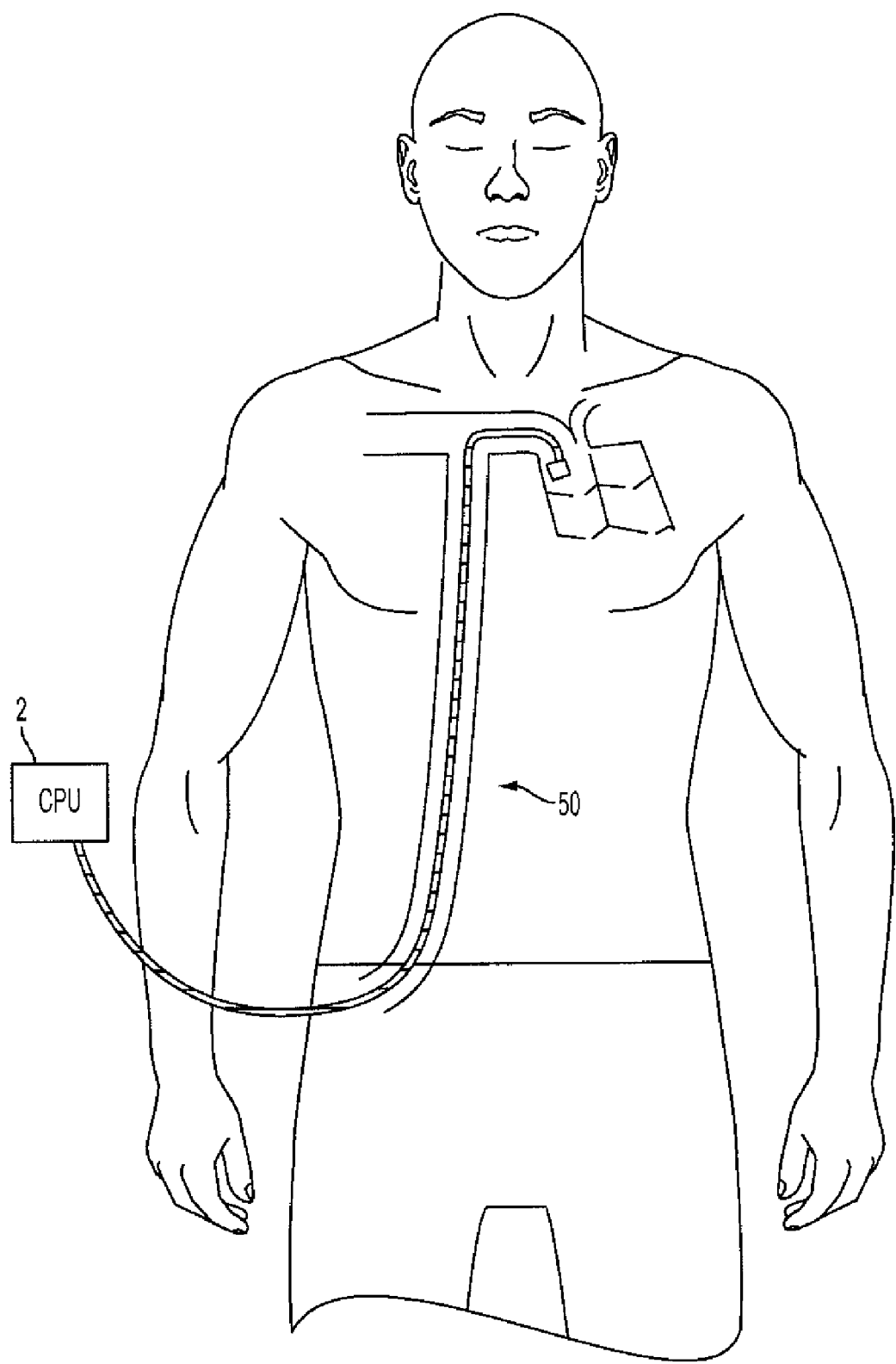
FIG. 4 is a representation of the apparatus of the present invention.

The catheter 1 preferably has radiopaque markings 88, as shown in FIG. 2, in proximity to the tip to identify location and distance of the catheter 1 in the patient. Preferably, the apparatus 50 includes a computer 2 in communication with the radiodetector 5 which analyzes information from the radiodetector 5. The bioptome 52 preferably includes an upper jaw 6 and a lower jaw 7, as shown in FIGS. 2 and 3. The radiodetector 5 can be disposed inside the catheter 1, with the upper jaw 6 on top of it, or outside the catheter 1 positioned approximately over the upper jaw 7. The radiodetector 5 basically should be positioned in relation to the jaw that is fixed.

The present invention pertains to a method for diagnosing a patient. The method comprises the steps of moving a tip of a catheter 1 to a desired location in a blood vessel 100 of the patient determined by radiation detected by a radiodetector 5 disposed in proximity to the tip. There is the step of obtaining a tissue sample of the patient with a bioptome 52 disposed in proximity to the tip.

There is preferably the step of identifying location and distance of the catheter 1 in the patient using radiopaque markings 88 in proximity to the tip. Preferably, there is the step of analyzing information from the radiodetector 5 with a computer 2. The obtaining step preferably includes the step of obtaining the tissue sample at a location of highest radiation in the patient as analyzed by the computer 2.

In the operation of the invention, the radiation detection catheter/bioptome comprises multiple components:
1) Catheter 1
2) Bioptome 52
3) Radiation detector 5
4) Equipment (computer) readout of radiation 2
5) Labeled radiotracer
1) The catheter 1 employed will be small enough to fit in the major veins of the body similar to the size of a central venous catheter. The catheter 1 must be pliable to maneuver in the ventricles and similar structures in the body.
2) Bioptome 52 will be a device attached or part of the catheter 1 itself located most distally on the catheter 1. The primary use of this will be to obtain tissue sample from the site being tested.
3) Radiation detector 5 will be attached or part of the catheter 1 itself located also distally on the catheter 1 as part of the bioptome 52 or a separate entity on the distal most portion of the catheter 1. The device will be used to locate the source of highest radiation.
4) Equipment including cables and a computer 2 will be necessary to interpret the readings from the catheter 1 into a readable format.
5) The labeled radiotracer will be one which is already employed, similar or the same as 18-Fluorodeoxyglucose. This will be injected into the patient and after a predetermined time the catheter 1 will be inserted to determine areas of increased uptake. The labeled marker will usually compromise at least two components: a detectable and a binding substance. The detectable markers can be radionuclides which emit beta radiation, conversion electrons, and, or gamma radiation. Preferred are radiolabels which emit beta radiation or those radionuclides that have a relatively short path length and permit precise localization of the target site.

Directions:

A catheter 1 that is employed with a bioptome 52 at the distal most portion with a radiodetector which will be part of or a separate entity attached at the distal portion of the catheter 1 will be used to detect and biopsy a target site of interest (FIG. 1). The catheter 1 will have radiopaque markings on the catheter 1 to identify location and distance (FIG. 2).

The catheter 1 will be inserted into a blood vessel or lumen and will be guided fluoroscopically or by other radiographic techniques into the general area of interest. The catheter's 1 radiodetector 5 will pick up the radiolabeled nucleotide injected into the vasculature.

The level of nucleotide will be measured by the detector 5 which is hooked up to the catheter 1 at the distal-most end. The detector will be hooked up through the catheter 1 by a wire or cable to transmit received signals to a processor or computer 2 to read the amount of radiation detected.

Once the catheter 1 is guided into the area of interest fluoroscopically, the radiation detector 5 will determine area(s) of highest measurement of labeled radiotracer.

The area(s) which is determined as the highest measurement will be biopsied by the bioptome 52, which is located on the most distal area of the catheter 1 as either part of the bioptome 52/catheter 1 unit, or as another piece connected to the distal most part of the catheter 1.

The device relies in part on previous patents, all of which are incorporated by reference herein:

The injection of radiolabeled lipoproteins into a patient where the lipoproteins are taken up into regions of atherosclerotic lesions to permit early detection of those lesions. U.S. Pat. No. 4,660,563.

Description of an intravascular radiation catheter. U.S. Pat. No. 5,811,814.

Methods and apparatus for characterizing lesions in blood vessels and other body lumens. European Patent No 1220691.

The present invention will find particular use in the identification of specific sites needed to biopsy. An example of which may be right ventricular biopsies currently done to identify the etiology of myocarditis. Currently biopsies are done randomly of the right ventricle and the etiology of myocarditis may not be found as the precise location of involvement is not known.

The innovation involves making and using a catheter 1 equipped with a bioptome 52 and a radiation detector 5 in conjunction with the detection of the lesion. With the ability to locate areas of interest and sample them at the precise location enables the ability to correctly obtain a diagnosis.

The radiation detector biopsy catheter employs a catheter 1 that will enter the lumen of a body and detect radiation and be able to biopsy at specific locations, specifically the location of highest radiation reading.

Known bioptomes have several disadvantages. Existing bioptomes are not able to detect with accuracy the area of interest to sample. This may lead to complications such as bleeding, damage to the tissue, and even death of an invasive procedure when the diagnosis is unsure.

In the figures, a radiation bioptome catheter 1 is described.

FIG. 1 shows the catheter 1 connected with the signal processor and computer processing unit 2 to read the level of radiation proximally. The proximal end of the catheter 1 also contains the mechanism for opening and closing the biopsy catheter 1 referred to as the tongs 3. A mechanism for allowing the operator to turn the catheter 1 in different locations is located slightly distal to the tongs 4. The distal end of the catheter 1, the end containing the radiation bioptome catheter 1, is shown entering the skin and then the blood vessel. This catheter 1 can be adapted in general to fit any lumen as it does to a blood vessel.

The radiation bioptome catheter 1 includes a flexible catheter 1 which can be remotely steered. The steering portion is located proximally. The dial 4 allows for the catheter 1 to move in a 360 degree fashion while the catheter 1 is advanced mechanically by the physician.

The distal portion of the radiation bioptome catheter 1, referring to FIGS. 2 and 3, is composed of the radiation detector 5 on one side. The distal portion of the radiation detector 5 will be employed with a jaw cutting device. The jaw device is composed of two opposing jaws, the upper fixed jaw 6 and the lower movable jaw 7. Fixed jaw is coupled to an attachment post 8 on the distal end of the catheter 1. Coupled refers to two components that attached (movably or fixed) directly by one or more intermediate components. The other end of fixed jaw 6 consists of a rounded end 9 with an internal hemispherical cup 10. The leading edge 11 of the fixed jaw 6 is sharpened so as to permit cutting and removal of tissue. Hinged jaw 7 is attached to fixed jaw 6, and includes a rounded end 12 with a hemispherical cup 13 as well as a sharpened leading edge 14. The other end of hinged jaw 7 rests within a slot 15 in fixed jaw 6. Hinged jaw pivots about a pin 16 securing end 17 of hinged jaw 7 into a slot 15. A clevis 18 is attached to hinged jaw 7 and to jaw actuation cable 19. When cable 19 is pulled, cable 19 pulls clevis 18 toward end cap of catheter 1. Hinged jaw 7 then pivots about pin 16 and opens jaw 6 and 7. Similar to existing bioptomes fixed jaw 6 and hinged jaw 7 can be brought together to pinch and then cut a piece of tissue 90. The cut tissue is retained in a cavity formed by the cups 10 and 13.

The distal portion of the radiation bioptome also contains the radiodetector 5. The radiodetector will be attached via pin 21 attached to a plate 22 on radiation detector 5. The plate 22 will attach to the securing end of fixed jaw 17 proximal to the radiation bioptome prior to the attachment of plate 22. This plate 22 will attach around the detector 5 and through the pin 16 on the fixed jaw 17.

A guidewire is used to guide the distal portion of the catheter to a region of interest of the blood vessel or lumen of interest. The guidewire is inserted using a guidewire insertion catheter. When the guidewire is positioned to extend slightly beyond the region of interest the guidewire insertion catheter is withdrawn leaving the catheter in place. The distal portion of the catheter slides along the guidewire.

As the distal portion of the catheter is advanced along the guidewire in the closed position through the blood vessel or lumen of interest the apparatus provides a continuous measure of radiation intensity detected by the radiation detection 5 assembly. The detected radiation is converted to a relative measure of radiation by the radiation measurement assembly 2 (CPU). The radiation measurement assembly 2 includes an output display or device or monitor. The monitor permits the physician to continuously monitor changes in radiation level as the distal portion of the catheter is advanced through the blood vessel.

Additionally, the advancement of the distal portion of the catheter may be viewed on a fluoroscopy screen. The area of interest involves looking at the radiopaque markings 88 on the catheter which will be able to be seen on the fluoroscopy screen. The radiation emitted by the particles injected into the patient's blood stream will also be able to be detected one by the fluoroscopy screen and two quantitatively by the radiation measurement assembly. This will allow the physician to appropriately guide the catheter to the area of interest for sampling.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for diagnosing a patient comprising:
a catheter comprising a distal end and a proximal end;
a bioptome disposed at the distal end of the catheter and configured to obtain a tissue sample of the patient when used, the bioptome comprising:
an attachment post fixably connected to the distal end of the catheter, and
an upper jaw connected to the attachment post and comprising a distal portion comprising a leading edge; and
a radiodetector positioned within the catheter and fixedly connected to the upper jaw and configured to detect, when used radiation in tissue proximal to the leading edge of the upper jaw.

2. The apparatus of claim 1 wherein the distal end of the catheter comprises radiopaque markings configured to identify a location of the catheter within the patient.

3. A method for diagnosing a patient comprising the steps of:
placing a distal end of a catheter comprising a bioptome within a lumen of the patient, the catheter comprising:
a bioptome comprising an attachment post fixably connected to the distal end, and an upper jaw connected to the attachment post and comprising a distal portion comprising a leading edge, and
a radiodetector positioned within the catheter and fixedly connected to the upper jaw and configured to detect radiation in tissue proximal to the leading edge of the upper jaw;
guiding the distal end of the catheter through the lumen;
via the radiodetector, continuously measuring radiation intensities of areas proximal to the leading edge of the bioptome as the catheter advances through the lumen;
identifying, based on the measured radiation intensities, an area of interest comprising an area of highest radiation; and
via the bioptome, obtaining a tissue sample from the area of interest.

4. The apparatus of claim 1, wherein the upper jaw further is fixably connected to the attachment post and comprises a rounded top portion and a bottom portion having an internal hemispherical cup.

5. The apparatus of claim 4, wherein:
the bioptome further comprises a pivotable lower jaw comprising a top portion having a hemispherical cup, a rounded bottom portion, and a distal portion comprising a leading edge; and
the lower jaw pivotally connects to the upper jaw, and pivots relative to the upper jaw.

6. The apparatus of claim 5, further comprising:
a clevis attached to the lower jaw; and
a jaw actuation cable attached to the clevis,
wherein the clevis and cable are configured so that when the cable is pulled, the lower jaw and the upper jaw open.

7. The apparatus of claim 1, further comprising a computer configured to analyze the radiation of the tissue sample being obtained.

8. The method of claim 3, further comprising identifying location and distance of the catheter in the lumen using radiopaque markings that are in proximity to the distal end.

* * * * *